United States Patent [19]

Wang et al.

[11] 4,391,720
[45] Jul. 5, 1983

[54] BIS(HYDROXYLKYL)DISILOXANES AND LUBRICANT COMPOSITIONS THEREOF

[75] Inventors: Chih C. Wang, Hightstown; Ronald F. Bates, Trenton, both of N.J.

[73] Assignee: RCA Corporation, New York, N.Y.

[21] Appl. No.: 408,502

[22] Filed: Aug. 16, 1982

Related U.S. Application Data

[62] Division of Ser. No. 231,859, Feb. 5, 1981, Pat. No. 4,355,062.

[51] Int. Cl.³ .............................................. C10M 1/50
[52] U.S. Cl. .................................................. 252/49.6
[58] Field of Search ................................. 252/27, 49.6

[56] References Cited

U.S. PATENT DOCUMENTS

| | | | |
|---|---|---|---|
| 2,951,861 | 9/1960 | Kerschner et al. | 252/49.6 X |
| 2,983,744 | 5/1961 | Knoth, Jr. | 260/448.2 |
| 3,308,147 | 3/1967 | Lentz | 252/49.6 X |
| 3,308,148 | 3/1967 | Hahn et al. | 252/49.6 X |
| 3,833,408 | 9/1974 | Matthies | 117/217 |
| 3,842,194 | 10/1974 | Clemens | 178/6.6 A |
| 4,025,693 | 5/1977 | Milne | 428/447 |
| 4,228,050 | 10/1980 | Martin et al. | 260/23 XA |
| 4,275,101 | 6/1981 | Wang et al. | 369/286 |

*Primary Examiner*—Andrew Metz
*Attorney, Agent, or Firm*—Birgit E. Morris

[57] ABSTRACT

Bis(hydroxyalkyl)disiloxane lubricants of the formula

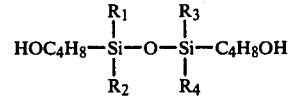

wherein $R_1$ and $R_3$ are methyl or ethyl and $R_2$ and $R_4$ are linear alkyl groups of up to 20 carbon atoms. These compounds are useful as additives to methyl alkyl siloxane lubricants for conductive high density information discs. Discs lubricated with the lubricant mixture exhibit improved stability to environments of high temperature and high relative humidity.

6 Claims, No Drawings

BIS(HYDROXYLKYL)DISILOXANES AND LUBRICANT COMPOSITIONS THEREOF

This is a division, of application Ser. No. 231,859, filed Feb. 5, 1981 now U.S. Pat. No. 4,355,062.

This invention relates to a lubricant additive for high density information records. More particularly, this invention relates to novel bis(hydroxyalkyl)disiloxanes that improve the playback performance of high density information records.

BACKGROUND OF THE INVENTION

Clemens, in U.S. Pat. No. 3,842,194, incorporated herein by reference, has disclosed a system for recording and playback of information including audio, video and color information capacitively. The high density information record has signal information in the form of a surface relief pattern in an information track, e.g., a spiral groove, on the surface of a disc. The disc is made conductive with a metal layer which acts as a first electrode of a capacitor, and which is coated with a dielectric layer and played back by means of a stylus electrode, which is the second electrode of the capacitor. Matthies, in U.S. Pat. No. 3,833,408 also herein incorporated by reference, discloses a methyl alkyl siloxane lubricant useful for the disc. The lubricant reduces friction between the disc and the stylus and thus reduces stylus wear.

Improvements made to the system since its early development include making a disc from a conductive plastic material made by adding conductive carbon black particles to a PVC matrix. This eliminated the need for separate metal and dielectric layers on the disc. The lubricant has also been improved by selecting a fractionated, purified methyl alkyl siloxane material. This has been disclosed by Wang et al in copending application Ser. No. 065,065, filed Aug. 9, 1979 now U.S. Pat. No. 4,275,101. This material has the formula

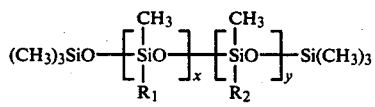

wherein $R_1$ and $R_2$ are alkyl groups of 4-20 carbon atoms, x is an integer of 2-4 and y is an integer of 0-2 and wherein the sum of x and y is 4 or less. The improved lubricant has better long term stability and improved first play performance.

One of the problems of the above described discs has been a sensitivity to degradation in the presence of water. When a carbon-loaded PVC disc is stored in or cycled through a warm, wet environment, a thin layer of solids, including organic and inorganic salts, forms on the surface of the disc, probably caused by various incompatible additives and products of degradation bleeding to the surface. When droplets of water deposit on the surface, these salts dissolve in the droplet. When the water evaporates, a nodule of salt is left behind that interferes with playback. When the stylus reaches such a deposit, it must ride over it whereupon the playback is interrupted, resulting in a loss of signal. In extreme cases, the stylus locks in the information track or skips a number of information tracks. These phenomena are called carrier distress which is measured as seconds of playback time during which signal information is lost. This problem has been somewhat alleviated by cleaning the discs after molding which removes the materials on the surface. However, with time, additional materials bleed to the surface or are formed on the surface due to oxidation reactions and the like, and carrier distress recurs, particularly after several cycles of water deposition and drying on the disc surface.

SUMMARY OF THE INVENTION

We have discovered bis(hydroxyalkyl)disiloxanes which are lubricants in themselves and which, when added to known disc lubricants as a dopant, reduce carrier distress without adverse effects on the playback performance or long term stability of the surface of high density information records.

DETAILED DESCRIPTION OF THE INVENTION

The bis(hydroxyalkyl)disiloxane compounds of the invention have the formula

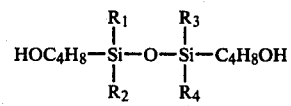

wherein $R_1$ and $R_3$ can be methyl or ethyl, preferably methyl, and $R_2$ and $R_4$ are linear long chain alkyl groups of up to about 20 carbon atoms. When the bis(hydroxyalkyl)disiloxanes are to be employed as a lubricant additive for high information video discs, the additives should be liquid. Mixtures of the above compounds wherein the alkyl groups have varying chain lengths are also useful, again with the proviso that the mixture be a liquid when employed as an additive for video disc methyl alkyl siloxane lubricants.

The bis(hydroxyalkyl)disiloxanes of the invention can be made according to the following sequence of steps in known manner, as described in Eaborn, Organosilicon Compounds, Butterworths Scientific Publications, London, 1960, pp. 299 and 304; Knoth et al, J. Am. Chem. Soc. 80, 1958, p. 4106; and Bazant et al, Organosilicon Compounds, Academic Press, New York, 1965, p. 260:

(1) a dichlorodialkylsilane is reacted with a heterocyclic ethylene oxide, such as tetrahydrofuran, according to the equation $$R_1R_2SiCl_2 + CH_2CH_2CH_2CH_2\text{-O} \longrightarrow R_1R_2Si(Cl)-O-(CH_2)_4Cl$$

(2) the product of step (1) is heated in the presence of an alkali metal (Me) such as lithium, potassium or sodium, or an alkaline earth metal such as magnesium to form the corresponding 1-oxa-2-silacycloalkane according to the equation

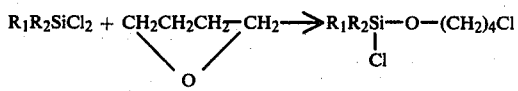

(3) the product of step (2) is hydrolyzed in the presence of an acidic catalyst such as HCl to form the desired bis(hydroxyalkyl)disiloxane compound according to the equation

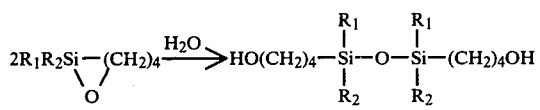

In the equations, $R_1$ and $R_2$ have the meanings given above.

The bis(hydroxyalkyl)disiloxane product can be purified for use as an additive for the video disc lubricant by distillation, preferably molecular distillation, collecting the distilland at about 100° C. The distillate will contain the more volatile ingredients such as HCl, unreacted oxasilocycloalkanes and other by-products and impurities.

The above described compounds can be added to the preferred video disc methyl alkyl siloxane lubricant in varying amounts. Generally no effect is obtained by adding amounts of less than about 5 percent by weight of the methyl alkyl siloxane lubricant and additive amounts of about 10–20 percent by weight are preferred. However, higher amounts, up to about 70 percent by weight of the methyl alkyl siloxane lubricant, can be employed.

The present compounds are boundary type lubricants, whereas the methyl alkyl siloxane lubricants of the prior art are primarily hydrodynamic lubricants. In the presence of large amounts of salts or other debris, e.g., dust particles, on the surface of the disc, the methyl alkyl siloxane lubricant becomes separated from the surface of the disc. The addition of the present bis(hydroxyalkyl)disiloxanes improves the ability of the lubricant system to lubricate the disc surface.

The present bis(hydroxyalkyl)disiloxanes are soluble in methyl alkyl siloxane lubricants described in Wang et al, and thus they can be readily applied together either by spraying from a solvent or by evaporating or by direct application. The disiloxanes are insoluble in water and thus the presence of water in the atmosphere has no effect on them. The bis(hydroxyalkyl)disiloxanes have low volatility so that they will not evaporate from the surface with time; they are not flammable and they have a very low melting point, i.e., less than about $-25°$ C., so that they will not solidify on the surface of the disc. In addition, they have a low surface tension so that they will wet the highly irregular surface of the disc in a uniform manner.

The invention will be further illustrated by the following Examples, but the invention is not meant to be limited to the details described therein. In the Examples percent is by weight unless otherwise noted.

Carrier distress time is measured by adding the amount of time in seconds (but discounting intervals of less than 10 microseconds) during disc playback when the r.f. output of the player arm is less than 150 millivolts peak to peak, and the time when the r.f. output gives above 8.6 megahertz or below 3.1 megahertz in frequency, indicating a defect. Such defects are noted by the viewer as dropouts. The present acceptable level of carrier distress for a video disc is 3 seconds in one hour of playback time.

EXAMPLE 1

Part A—Preparation of methyl decyl dichlorosilane 2.25 Parts of methyl dichlorosilane, 4.04 parts of 1-decene and a solution containing about 0.0005 part of chloroplatinic acid catalyst in 0.006 part of 2-propanol were charged to a reaction vessel and heated to about 100°–120° C. for six hours. The product was vacuum distilled in 110°–114° C. at 1–3 Torr. 4.7 Parts (94% yield) of methyl decyl dichlorosilane was obtained.

Part B—Preparation of 2,2-methyl decyl-1-oxa-2-silacyclohexane

The product from Part A was charged along with 6.4 parts of tetrahydrofuran, 0.454 part of magnesium, 0.078 part of methyl iodide and 0.0015 part of iodine to a reaction vessel. The mixture was refluxed at 85° C. for 24 hours.

The reaction mixture was transferred to a separation vessel, and 11 parts of water were added to dissolve the magnesium chloride byproduct. The organic portion was collected, stripped of volatiles in a rotary evaporator at 80° C. and about 10 Torr for one hour, the remaining portion was distilled with about 0.002 part of KOH at about 170° C. and 2 Torr for 6 hours, and finally purified by fractionally distillating at 1 Torr and collecting the fraction at 130°–140° C.

2,2-methyl decyl-1-oxa-2-silacyclohexane was obtained in a yield of 63.8% (3.2 parts).

Part C—Preparation of 1,3-bis(4-hydroxybutyl)-1,3-dimethyldodecyldisiloxane

The product from Part B was hydrolyzed with 7.2 parts of water in 3.2 parts of tetrahydrofuran by refluxing for about 16 hours. A small amount of HCl (0.0014 part) was added as catalyst and 0.0065 part of triethylamine added at the end to neutralize the acid and quench the reactions. The organic and aqueous layers were separated.

The organic phase was purified by vacuum stripping at 90° C. under 2 Torr for one hour.

The product was molecularly distilled at 100° C. under $10^{-3}$ Torr and the distilland collected. The overall yield was 2.9 parts (60%).

The structure was confirmed by elemental analysis, infrared, absorption spectroscopy, gel permeation chromatography, gas phase chromatography and mass spectroscopy which confirmed the molecular weight as 530.

Elemental analysis was C, theoretical 67.92; found, 68.39; H, theoretical 12.45; found, 12.56; Si, theoretical 10.56; found, 10.42. Only 20 ppm of N and 50 ppm of Cl were detected. Trace amounts of Mg and Fe (total 10 ppm) were found by emission spectroscopy.

The product was a liquid having a surface tension of 28 dynes/cm at 25° C.; a specific gravity of 0.89 gram per milliliter at 25° C.; a refractive index of 1.461; and a viscosity of $150\pm5$ centipoises at 25° C. It did not volatilize after storage for 24 hours under a vacuum of $10^{-6}$ torr at 22° C., or after 24 hours storage at 100° F. and 1 atmosphere. No polymerization or hydrolysis occurs under ambient conditions. The pour point is below $-25°$ C. and the flash point is above 300° F. The product is completely soluble in heptane and in the methyl alkyl siloxane of the formula

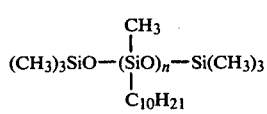

which is the product of molecular distillation at 205° C. It is insoluble in water.

Part D—Application to high density information discs

The disiloxane as prepared in Parts A to C was dissolved as a 0.06 percent solution in heptane and sprayed onto conductive video discs which are described by Martin et al in U.S. Pat. No. 4,228,050. The discs exhibited good initial play with an average carrier distress range of about 0-0.5 second in 30 minutes of play.

The discs were stressed by placing in a chamber held at 95 percent relative humidity and 100° F. for one hour. The discs then had carrier distress levels of less than 1 second in 30 minutes of play.

Repeated play resulted in some redistribution of the lubricant on the surface of the disc.

EXAMPLE 2

The disiloxane as prepared in Example 1 Parts A to C was dissolved in heptane to a 0.06 percent by weight solution and mixed with a 0.06 percent solution of the purified methyl alkyl siloxane lubricant as described hereinabove in heptane in a ratio of 80:20 of lubricant to dopant. This solution was sprayed onto 12 video discs. On initial play, 8 discs had carrier distress levels of less than 0.3 second, 3 had carrier distress levels of 0.4-1 second and 1 disc had carrier distress in the range of 1.1-3 seconds.

After stressing as in Example 1 Part D, 9 discs had less than 1 second of carrier distress, 2 discs were in the range of 1-3 seconds and 1 disc had carrier distress in the range of 3-10 seconds.

These discs were compared to a similar series of 12 discs lubricated with the purified methyl alkyl siloxane lubricant alone. In initial play, 8 discs had carrier distress of less than 0.3 second, 2 discs had carrier distress levels in the range 0.4-1 second, 1 disc had carrier distress in the range 1.1-3 seconds and 1 disc had carrier distress in the range of 3.1-10 seconds.

After condensation stressing, however, only 5 discs had carrier distress within the range of 0-1 second, 1 disc had carrier distress of 1-3 seconds, 4 discs had carrier distress in the range of 3-10 seconds, 1 disc had carrier distress of 10-30 seconds and 1 disc had carrier distress of over 100 seconds.

Thus the methyl alkyl siloxane lubricant containing the bis(hydroxyalkyl)disiloxane additive somewhat reduces the level of carrier distress on initial play but greatly reduces carrier distress after condensation stressing.

EXAMPLE 3

The procedure of Example 2 was repeated on another series of video discs in lots of six discs each that had been cleaned in dilute Shipley cleaning solution according to the procedure of Nyman et al, Ser. No. 091,878 filed Nov. 7, 1979, and dried in 1,1,2-trifluoro-2,2,1-trichloroethane according to the procedure of Nyman et al, Ser. No. 165,977 filed July 7, 1980, both herein incorporated by reference. These discs were played once and condensation stressed twice. They were compared to cleaned and dried discs coated only with the purified methyl alkyl siloxane lubricant. The results are tabulated below.

| Disc Lot # | Initial Play | | After Stress 1 | | After Stress 2 | |
|---|---|---|---|---|---|---|
| | Median | Range | Median | Range | Median | Range |
| DOPED LUBRICANT Carrier Distress, secs./hour | | | | | | |
| 1 | 0.1 | 0.0-1.3 | .8 | .2-3.4 | 0.6 | 0.0-1.2 |
| 2 | 0.2 | 0.0-0.3 | .7 | 0.0-15.6 | 0.5 | 0.0-1.0 |
| 3 | 0.2 | 0.0-1.3 | 0.4 | 0.0-1.2 | 0.7 | 0.0-0.8 |
| 4 | 0.35 | 0.0-11.6 | 0.4 | 0.0-1.0 | 0.5 | 0.0-0.8 |
| 5 | 1.9 | 0.0-7.1 | 0.7 | 0.2-1.6 | 0.4 | 0.2-1.0 |
| | 0.5 | | 0.6 | | 0.5 | |
| UNDOPED LUBRICANT Carrier Distress, secs./hour | | | | | | |
| 3 | 0.75 | 0.0-18.2 | 1.0 | 0.8-2.6 | 1.5 | 0.0-316.6 |
| 4 | 0.35 | 0.0-10.9 | 0.8 | 0.0-7.6 | 1.7 | 0.0-9.4 |
| 5 | 0.45 | 0.0-22.6 | 3.1 | 0.6-13.4 | 3.1 | 0.2-24.8 |
| | 0.5 | | 1.6 | | 2.1 | |

Thus the doped lubricant reduces the carrier distress after stressing.

Stylus wear was tested by playing some of the above discs for 44 hours and the lubricant only and doped lubricant discs compared. The results were similar.

EXAMPLE 4

Five discs each were sprayed directly with standard lubricant and doped lubricant containing 20 percent by weight of the dopant. The discs were played once, stressed as in Example 1 and played again. The carrier distress data is shown below.

| Disc # | CARRIER DISTRESS, secs./hour | | | |
|---|---|---|---|---|
| | Initial Play | | After Stress 2 | |
| | Undoped | Doped | Undoped | Doped |
| 1, side 1 | 1.55 | .15 | 40.1 | .05 |
| side 2 | .10 | .15 | 6.5 | .05 |
| 2, side 1 | .14 | .10 | 40.5 | .70 |
| side 2 | .08 | .05 | 20.1 | .05 |
| 3, side 1 | .23 | .41 | 2.6 | .28 |
| side 2 | .13 | .29 | 3.1 | .17 |
| 4, side 1 | .27 | .75 | 75.8 | .52 |
| side 2 | .14 | .20 | 179.7 | .22 |
| 5, side 1 | .45 | .05 | 186.0 | 1.20 |
| side 2 | 17.10 | .05 | 6.2 | .05 |

We claim:
1. A composition comprising a solution of a methyl alkyl siloxane lubricant of the formula

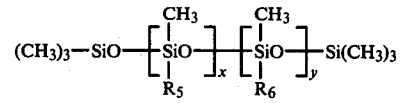

wherein $R_5$ and $R_6$ are alkyl groups of 4 to 20 carbon atoms, x is an integer of 2-4, y is an integer of 0-2 and wherein the sum of x and y is 4 or less, containing from about 5 percent to about 70 percent by weight of the lubricant of a compound of the formula

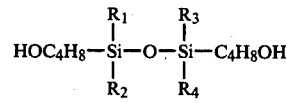

wherein $R_1$ and $R_3$ are methyl or ethyl and $R_2$ and $R_4$ are linear alkyl groups of up to 20 carbon atoms.

2. A composition according to claim 1 wherein the lubricant contains from about 10 percent to about 20 percent by weight of the bis(hydroxyalkyl)disiloxane of claim 1.

3. A composition according to claim 1 wherein $R_1$ and $R_3$ are methyl.

4. A composition according to claim 1 wherein $R_2$ and $R_4$ are $C_8$-$C_{12}$.

5. A composition according to claim 1 wherein $R_1$ and $R_3$ are methyl and $R_2$ and $R_4$ are $C_{10}H_{21}$.

6. A composition according to claim 2 wherein $R_1$ and $R_3$ are methyl and $R_2$ and $R_4$ are $C_{10}H_{21}$.

* * * * *